United States Patent
Park et al.

(10) Patent No.: US 6,280,806 B1
(45) Date of Patent: *Aug. 28, 2001

(54) BRAUN TUBE HAVING ANTIBACTERIAL COATING FILM

(75) Inventors: Jae-huy Park; Dae-in Park; Bum-je Jeaun; Su-Jin Han, all of Pusan; Jin-nam Kim, Kyungsangbuk-do, all of (KR)

(73) Assignee: Samsung Display Devices Co., Ltd., Kyungki-Do (KR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/072,985

(22) Filed: May 6, 1998

(30) Foreign Application Priority Data

May 6, 1997 (KR) .................................................. 97-17235

(51) Int. Cl.[7] ..................................................... H01J 31/50
(52) U.S. Cl. ..................... 428/34.4; 428/34.6; 428/36.91; 313/479; 313/480; 348/824; 348/834
(58) Field of Search ................................. 313/477 R, 479, 313/480, 110, 111, 112; 348/824, 834; 428/325, 331, 336, 333, 689, 36.91, 34.6, 34.4

(56) References Cited

U.S. PATENT DOCUMENTS 5,667,729 * 9/1997 Shimbori .............................. 252/508
5,755,867 * 5/1998 Chikuni et al. .................. 106/287.16

* cited by examiner

*Primary Examiner*—Rena L. Dye
(74) *Attorney, Agent, or Firm*—Leydig, Voit & Mayer, Ltd

(57) ABSTRACT

A Braun tube having an antibacterial coating film, which is manufactured by the steps of dispersing titanium dioxide ($TiO_2$) in alcohol to prepare a dispersion. Then, the dispersion is coated on a Braun tube, and a thermal treatment is then performed. By a photocatalytic reaction of the titanium dioxide contained in the antibacterial coating film, oxygen ($O_2$) and water ($H_2O$) in the air are decomposed into superoxides ($O^{2-}$) and hydroxy radicals ($OH\cdot$), which destroy bacteria and mold around the Braun tube and remove bad odor.

3 Claims, No Drawings

BRAUN TUBE HAVING ANTIBACTERIAL COATING FILM

BACKGROUND OF THE INVENTION

1. Field of the Invention

The present invention relates to a Braun tube and a manufacturing method therefor, and more particularly, to a Braun tube having an antibacterial coating film and a manufacturing method therefor.

2. Description of the Related Art

A Braun tube can generate much heat and has electrifying properties. Thus, dust in air easily attaches to the Braun tube and various kinds of microorganisms can reside therein. To solve these problems, an antistatic treatment has been proposed.

Such antistatic treatment prevents the generation of static electricity, thus reducing attachment of dust thereto. However, the antistatic treatment can neither block the heat generated from the Braun tube nor prevent the propagation of microorganisms. Thus, problems relating to sanitation caused by the breeding of microorganisms remain. However, there has been no research at all into a technology for providing a function of preventing the propagation of microorganisms. Most of the research has focused on an antibacterial composition per se and application of the antibacterial composition to a fiber or a sanitary container. Also, most such antibacterial compositions are formed of organic substances.

SUMMARY OF THE INVENTION

To solve the above problems, it is an object of the present invention to provide a Braun tube having an antibacterial function.

It is another object of the present invention to provide a method for manufacturing the above Braun tube.

To achieve the first object, there is provided a Braun tube comprising an antibacterial coating film containing titanium dioxide ($TiO_2$).

Preferably, the thickness of the antibacterial coating film is in a range between 500~5,000 Å.

Preferably, the content of titanium dioxide with respect to the antibacterial coating film is between 5~10% based on weight.

Preferably, the antibacterial coating film further comprises at least one silicate compound. Here, the mixing ratio of the titanium dioxide and silicate compound may be in a range between 1:1~1:2, and the sum of the titanium dioxide and silicate compound may be in a range between 10~20% based on total weight of the antibacterial coating film. Also, the silicate compound may be methyl silicate, ethyl silicate or metal silicate.

Also, preferably, the titanium dioxide has a structure of anatase and the average particle diameter is in a range between 1~50 nm.

To achieve the second object, there is provided a method for manufacturing a Braun tube having an antibacterial coating film, comprising the steps of: (a) preparing a dispersion by dispersing titanium dioxide ($TiO_2$) in alcohol; and (b) coating the dispersion on the Braun tube and performing a thermal treatment.

Preferably, the titanium dioxide has a structure of anatase and the average particle diameter is in a range between 1~50 nm.

Preferably, the concentration of titanium dioxide in the dispersion is in a range between 5~10% based on weight.

Preferably, the coating is performed to a thickness in a range between 500~5,000 Å.

Also, preferably, the thermal treatment after the coating is performed at a temperature between 130~150° C. for 30~60 minutes.

Preferably, between the steps (a) and (b), the method further comprises the steps of: (a1) mixing the dispersion with a solution of silicate compound; and (a2) adjusting the pH of the mixture, re-dispersing the mixture using ultrasonic waves, and aging the dispersion. Here, the aging may be performed at a temperature between 30~60° C. for 30~60 minutes.

DESCRIPTION OF THE PREFERRED EMBODIMENT

Hereinafter, a method for manufacturing an antibacterial Braun tube and the operating principle thereof will be described in detail.

According to a preferred embodiment, an antibacterial Braun tube according to the present invention is manufactured by the following method.

First, titanium dioxide is dispersed in alcohol with a final concentration of 5~10% based on weight, to prepare a dispersion. Here, a dispersion of a silicate compound in alcohol or other solvents, is mixed with the above dispersion, and then the pH was adjusted to be acidic, preferably, pH 2~3, and the mixture is then dispersed for 10 minutes or more using ultrasonic waves of 10~50 kHz. Then, the resultant solution is subjected to a thermal treatment for aging at 30~60° C. for 30~60 minutes. By this aging, the silicate compound is partially polymerized, and the obtained polymer acts as a binder between the glass Braun tube and the antibacterial coating film in a subsequent process. The solution obtained through the above thermal treatment is coated on the Braun tube, and thermally treated to form an antibacterial coating film, thereby resulting in a Braun tube having an antibacterial coating film according to the present invention. Preferably, a general coating method such as spin coating, spray coating and deposition can be used, and the thermal treatment is performed at 130~150° C. for 30~60 minutes. During the thermal treatment, the solvent is completely vaporized from the composition coated on the glass surface, resulting in a hard and compact coating film containing silicon dioxide ($SiO_2$) and titanium dioxide ($TiO_2$).

Preferably, titanium dioxide ($TiO_2$), the major component of the antibacterial coating film of the present invention, has a structure of anatase and average particle diameter of 10~20 nm. Here, the particle size is determined in view of the coating properties and the solvent to be used and the agglomeration to silicate.

Also, preferably, the coating film has a thickness preferably between 500~5,000 Å. If the thickness of the coating film is less than 500 Å, the antibacterial effect thereof can be insignificant Meanwhile, if the thickness of the coating film is over 5,000 Å, which exceeds the normal thickness on the Braun tube, it can be difficult to form a uniform coating film.

If a silicate compound is additionally used, the coating properties and hardness of the coating film are desirably maintained in a mixing ratio of 1:1~1:2 between titanium dioxide and the added silicate compound based on weight.

The principle of the antibacterial function of the Braun tube having an antibacterial coating film according to the present invention manufactured by the above method is as follows.

By a photocatalytic reaction of the titanium dioxide contained in the antibacterial coating film of the Braun tube, oxygen ($O_2$) and water ($H_2O$) in the air are decomposed to generate. superoxides ($O^{2-}$) and hydroxy radicals ($OH\cdot$). Such decomposed products can kill bacteria and mold around the Braun tube, and remove bad odor. The photocatalytic reaction may be performed by light originated from sunlight, lighting or fluorescent lamp. Also, this reaction occurs by the light of the Braun tube itself. Thus, the antibacterial effect of the Braun tube having the antibacterial coating layer can be achieved. In detail, $O_2$ in the air is changed into $O^{2-}$ by electrons generated during which a Ti cation is formed from decomposition of $TiO_2$ by light, and the hydroxy group is changed into hydroxy radical. Such resultant substances adversely affects the metabolism and electron-transport system of microorganisms, thereby suppressing the propagation of bacteria or mold.

Hereinafter, the present invention will be described in detail with reference to an example. However, the present invention is not limited to the following example.

30 g of $TiO_2$ having the structure of anatase and an average particle diameter of about 30 nm was dissolved in 600 g of ethanol to obtain a dispersion. Then, 300 g of methyl silicate dispersion (10%) was added, and then uniformly mixed, and the pH of the solution was adjusted to approximately 4.5. Then, the mixture was dispersed for 15 minutes using ultrasonic waves of about 30 kHz, and aging process was performed at 35° C. for 40 minutes, resulting in an antibacterial coating composition. After spraying the antibacterial coating composition over the Braun tube, a thermal treatment was performed at 150° C. for approximately 1 hour to form a coating film having about a thickness of 1,000 Å, thereby completing a Braun tube according to the present invention. E. coli ($10^6/cm^2$) was inoculated on surfaces of antibacterial coating films of two Braun tubes illuminated with a fluorescent lamp. Also, the antibiotic coating film surfaces were continuously exposed to sunlight during daylight hours. Here, one of Braun tubes was turned on, and the other was turned off. After 24 hours, the number of E. coli alive was counted.

As a result, the number of E. coli on the Braun tube that was turned off decreased by 90% compared to the initial inoculation. The results were the same for the Braun tube that was turned on. That is, in the Braun tube according to the present invention, the number of E. coli was greatly decreased.

However, the number of E. coli might increase logarithmically for 24 hours, through several duplication cycles if the circumstance do not change unfavorably for growth of the microorganisms. Thus, it can be seen that the Braun tube of the present invention suppresses growth of microorganisms.

As described above, the Braun tube of the present invention exhibits high level of antibacterial function, so that it can be used effectively in an environmentally sanitary setting. Thus, the present invention can be applied to various fields requiring antibacterial characteristics, particularly, to a screen of a display device.

What is claimed is:

1. A Braun tube including an antibacterial film consisting of $TiO_2$ and a silicate in the ratio of about 1:1 to about 1:2.

2. A Braun tube including an antibacterial film consisting of $TiO_2$ and a silicate, wherein the $TiO_2$ has the structure of anatase and the average particle diameter is in the range of 1–50 nm.

3. A Braun tube including an antibacterial film consisting of $TiO_2$ and a silicate, wherein the thickness of the antibacterial coating film is in the range of 500–5000 Å.

* * * * *